United States Patent [19]
Juhasz et al.

[11] Patent Number: 5,561,678
[45] Date of Patent: Oct. 1, 1996

[54] TIME-SHARING LASER

[75] Inventors: Tibor Juhasz, Irvine; Laszlo Turi, San Diego, both of Calif.

[73] Assignee: Intelligent Surgical Lasers, San Diego, Calif.

[21] Appl. No.: 432,800

[22] Filed: May 2, 1995

[51] Int. Cl.⁶ ........................................................ H01S 3/10
[52] U.S. Cl. ............................................. 372/25; 372/12
[58] Field of Search ................................. 372/12, 25, 93

[56] References Cited

U.S. PATENT DOCUMENTS

| | | |
|---|---|---|
| H275 | 5/1987 | Milberger et al. |
| 3,572,897 | 3/1971 | Bousky . |
| 3,653,743 | 4/1972 | Kiefer et al. |
| 3,663,091 | 5/1972 | Lee . |
| 4,277,146 | 7/1981 | Morgan et al. |
| 4,439,861 | 3/1984 | Bradford . |
| 4,571,085 | 2/1986 | Anderson . |
| 4,620,113 | 10/1986 | Sizer, II et al. |
| 4,629,993 | 12/1986 | Bouvier et al. |
| 4,896,119 | 1/1990 | Williamson et al. |
| 5,001,716 | 3/1991 | Johnson et al. ............... 372/12 |
| 5,016,251 | 5/1991 | D'Arcy . |
| 5,221,988 | 6/1993 | Juhasz . |

OTHER PUBLICATIONS

Martin Gifford and Kurt J. Weingarten, *Diode-pumped Nd:YLF regenerative amplifier*, Optics Letters, vol. 17, No. 24, Dec. 15, 1992, pp. 1788–1790.

Vincent J. Newell et al., *Tunable subpicosecond dye laser amplified at 1 kHz by a cavity-dumped, Q-switched, and mode-locked Nd:YAG laser*, Optical Society of America, vol. 6, No. 2, Feb. 1989, pp. 257–263.

U. Ketter et al., *High-frequency acousto-optic mode locker for picosecond pulse generation*, Optics Letters, vol. 15, No. 1, Jan. 1, 1990, pp. 45–47.

Theodore Sizer, II and Iri N. Duling, III, *Neodymium Lasers as a Source of Synchronized High–Power Optical Pulses*, IEEE Journal of Quantum Electronics, vol. 24, No. 2, Feb. 1988, pp. 404–410.

L. Min et al., *Cavity Dumped Operation of a CW Pumped Q–Switched and Mode–Locked YLF Laser*, Optics Communications, vol. 68, No. 6, Nov. 15, 1988, pp. 427–430.

I. N. Duling, III et al., *A Simplified Method of Producing High Energy Nd:YAG Pulses at High Repetition Rates*, AT&T Technical Memorandum, Sep. 16, 1986.

Primary Examiner—Rodney B. Bovernick
Assistant Examiner—Robert E. Wise
Attorney, Agent, or Firm—Nydegger & Associates

[57] ABSTRACT

A system for generating a pulsed laser beam includes a laser source and a mode locker which are mounted in a housing that defines a beam path for light from the laser source. An electro-optical crystal is positioned on the beam path to selectively polarize light traveling along the beam path. In operation, the crystal is repetitively advanced through a three period working cycle. At the beginning of the no-lase period which initiates each working cycle, the electro-optical crystal is partially activated. After a predetermined period, pumping of the laser source begins. Next, in the pulse shaping or pre-lasing period, the mode locker becomes active to produce a single compressed pulse in the laser cavity. After pulse-shaping the system for approximately two-hundred and fifty to three-hundred microseconds, the electro-optical crystal is fully activated to start the amplification period to create an amplified laser pulse. The amplification period lasts for approximately two-tenths of one microsecond (0.2 µs) to one microsecond (1 µs). The crystal is then again deactivated to eject the amplified pulses from the cavity and initiate another working cycle.

17 Claims, 2 Drawing Sheets

TIME-SHARING LASER

FIELD OF THE INVENTION

The present invention pertains generally to pulsed laser beam generators. More particularly, the present invention pertains to a system for generating a pulsed laser beam for a high-gain system wherein the pulse-shaping, or pre-lasing, period is controlled to minimize the leakage of unamplified laser pulses from the generator. The present invention is particularly, but not exclusively, useful for generating pulsed laser beams which reduce the risk of unwanted tissue damage during ophthalmic laser surgery.

BACKGROUND OF THE INVENTION

In general, it is often desirable to change the natural duration of laser pulses produced by pulsed lasers. More specifically, the development of devices and apparatus which generate compressed or shortened laser pulses has been found to be advantageous for a plethora of applications. To this end, three basic mechanisms have been developed to produce compressed or shortened laser pulses. These basic mechanisms are mode-locking, Q-switching, and cavity-dumping. Traditionally, these three mechanisms have been employed as part of a separate low-power pulse generator. The laser output from the pulse generator is then fed into a regenerative amplifier where the energy of the individual pulses is amplified to become the overall laser output.

Practice has demonstrated, however, that the employment of lasers which include a pulse generator that is separate from the regenerative amplifier is subject to certain disadvantages. For example, it is often the case that the size and complexity of such systems has limited their applicability in real world situations. As a result, laser systems which include the basic pulse compression mechanisms within the laser cavity of the regenerative amplifier have received increasing attention. A laser of this type is described in an AT&T memorandum dated Sep. 16, 1986, authored by Dulling et al., in which it was suggested that the basic mechanisms of mode-locking, Q-switching, and cavity-dumping all be combined within the laser cavity of a regenerative amplifier.

So-called "all-in-one" pulsed laser beam generators, of the type proposed by Dulling et al., employ a time-sharing methodology where the single laser cavity is first used to generate a sequence of short-duration laser pulses. Once the pulse-shaping or pre-lasing period is complete, the laser cavity is used to regeneratively amplify the pulse train which becomes the laser output.

Inclusion of the basic mechanisms of mode-locking, Q-switching, and cavity-dumping within the laser cavity of a regenerative amplifier allows all-in-one laser systems to offer a compact layout which can be highly advantageous in real-world situations. It may be appreciated, however, that traditional methods for implementing these basic methods within the laser cavity may result in a laser system with an unacceptably high cost. More specifically, it may be appreciated that the functions of Q-switching and cavity dumping have traditionally been performed using separate active elements, each of which must be controlled and coordinated during the duty cycle of the laser system. This approach complicates the design of the all-in-one laser and may result in excessive system cost. For this reason, it is desirable to produce an all-in-one laser which combines the functions of Q-switching and cavity dumping within a single active element.

Unfortunately, all-in-one pulsed laser systems have certain operational characteristics which, if they are not properly controlled, can limit their efficacy. Specifically, substantial leakage of low intensity laser pulses can occur during the generation of a pulsed laser beam if the various mechanisms of the system are not effectively coordinated and employed. The primary cause of this leakage is due to system limitations which result from the requirement that, in order for mode-locking to occur, it is necessary that the laser medium be pumped to emit light. As a result, there is a tendency for the regenerative amplifier to prematurely amplify the pulse train before the pulse-shaping period has completed. In order to prevent a runaway amplification of the pulse train before completion of pulse-shaping, the tack has been to eject part of the pulse train from the laser cavity using a slightly misaligned quarter-wave plate ($\lambda/4$) on the cavity laser beam path. The result is that an uninterrupted train of pulses are emitted from the cavity. While some of this leakage may be acceptable, extensive leakage of laser pulses from the cavity, even though they be of low intensity, can have adverse effects in many applications. This is particularly so when the pulsed laser system is to be used for ophthalmic surgery.

The present invention recognizes that unwanted leakage of laser pulses from the laser cavity can be minimized by properly controlling the pumping of the laser medium. Specifically, rather than relying on misaligned quarter wave plates to prevent runaway amplification, the present invention recognizes that by pumping the laser medium in a quasi-continuous fashion during the period of pulse-shaping, runaway amplification may be avoided.

In light of the above, it is an object of the present invention to provide a pulsed laser beam generator which provides a high-frequency, high-power pulsed output. Another object of the present invention is to provide a pulsed laser beam generator which combines the basic pulse compression mechanisms and amplification means within a single laser cavity. It is still another object of the present invention to provide a pulsed laser beam generator which minimizes leakage of laser energy during the pulse-shaping process. Still another object of the present invention is to provide a pulsed laser beam generator which combines the functions of Q-switching and cavity dumping within a single active element. Yet another object of the present invention is to provide a pulsed laser beam generator which is relatively simple to use, relatively easy to manufacture, and comparatively cost effective.

SUMMARY OF THE PREFERRED EMBODIMENTS

In accordance with the present invention, a pulsed laser beam generator includes a means for generating pulses of laser light and a means for amplifying such pulses. More specifically, the pulsed laser beam generator of the present invention includes a housing formed with a cavity, and a pair of opposed end mirrors which are mounted in the housing cavity to establish an internal laser beam path. Positioned in the housing cavity on the internal beam path between the end mirrors are: a mode locker; a laser medium; a polarizing mirror; a quarter-wave ($\lambda/4$) plate; and an electro-optical crystal. A laser diode or an array of laser diodes is also mounted in the housing to pump the laser medium, and a voltage source is electrically connected to the electro-optical crystal to selectively activate the crystal.

In operation, the laser system of the present invention is repetitively advanced through a working cycle which may be subdivided into three periods: a no-lase or deactivated period, a pre-lasing or pulse-shaping period and a pulse-amplification period. As the no-lase period begins, the diode laser is in a deactivated state and no-pumping of the laser medium occurs. Additionally, at this time, a predetermined voltage is applied to the electro-optical crystal and the crystal becomes partially activated after a rise time of 100 µs. The degree to which the electro-optical crystal is activated depends on the particular laser medium employed but is generally less than the quarter-wave activation of which the electro-optical crystal is capable. Approximately three-hundred micro-seconds (300 µs) before the end of the no-lase period, the diode laser is activated to start pumping the laser medium. As a result, the gain of the laser medium increases and surpasses the relatively high losses in the laser cavity ending the no-lase period. It should be appreciated that the no-lase period may be varied in duration to alter the overall duration of the working cycle of the present invention. For example, in the case where the working cycle is to last one-millisecond (1 ms), or repeated at a one-kilohertz (1 Khz) rate of repetition, the no-lase period will be seven-hundred micro-seconds in duration (700 µs).

As the no-lase period ends, the working cycle enters the pre-lasing or pulse-shaping period. During the pulse-shaping period the electro-optical crystal remains partially activated and the diode laser continues to pump the laser medium. The pulse-shaping period will typically last approximately two-hundred and fifty to three-hundred microseconds (250 to 300 µs) and is necessary for the laser medium to first produce a train of laser pulse which are then combined into a single pulse of short duration by the mode-locker.

A pulse amplification period which lasts between approximately two-tenths of one microsecond (0.2 µs) approximately one microsecond (1 µs) immediately follows the pulse-shaping period. In this amplification period, the electro-optical crystal is fully activated to confine laser light pulse in the cavity. This fully activated condition for the crystal, and resultant confinement of light in the cavity, causes the confined laser light pulse to be amplified by its repeated passage through the pumped laser medium. Thus, an amplified laser pulse is generated.

When the laser pulse reaches its maximum energy the laser diode is switched off. Additionally, the electro-optical crystal is deactivated ejecting the amplified laser pulse from the cavity. This deactivation of the electro-optical crystal also ends the amplification period and initiates another working cycle. Accordingly, by repeatedly cycling the laser system through a series of working cycles, as disclosed above, a beam of amplified laser pulses is generated.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENT

Figure 1:
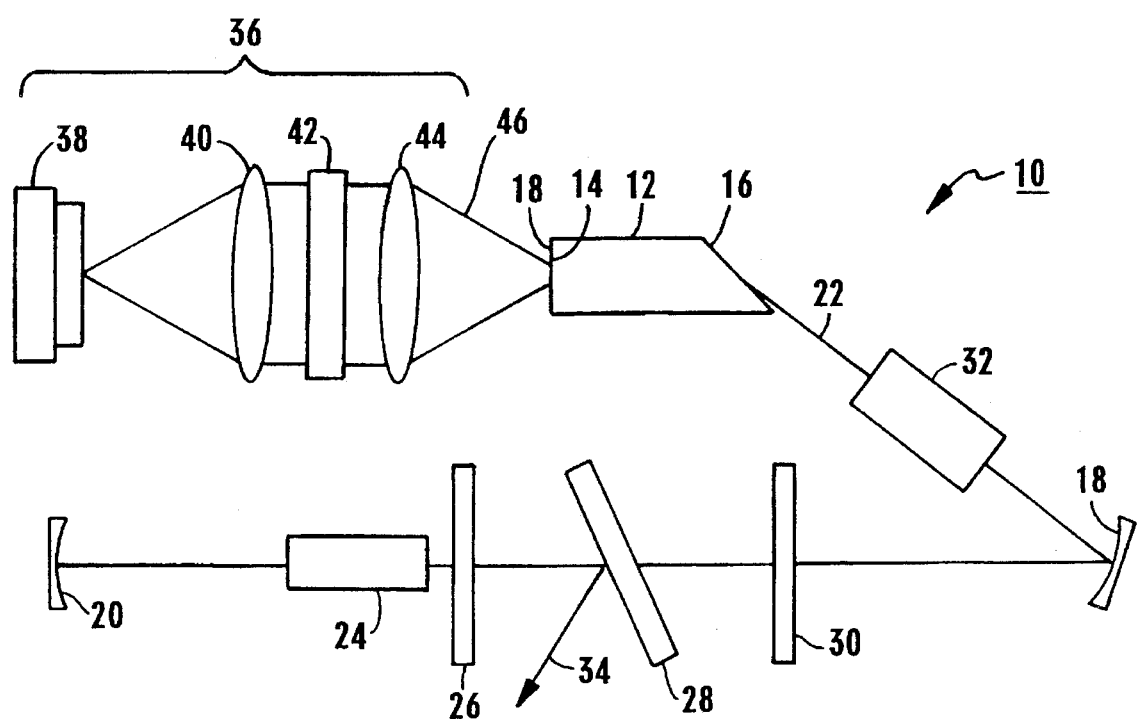
FIG. 1 is a schematic diagram of the components which comprise the laser pulse generator of the present invention.

The present invention provides a system and a method for generating a high-gain pulsed laser beam. The apparatus of the present invention is shown schematically in FIG. 1 and generally designated 10. As shown in FIG. 1, the apparatus 10 of the present invention includes a laser rod 12 preferably fabricated from a Nd:YLF rod doped at 1.1% Neodymium. The laser rod 12 is formed with a first end 14 and a second end 16. The first end 14 of the laser rod 12 is coated for high reflectivity at the wavelength which corresponds to the pi polarization of the laser rod 12. Specifically, for the Nd:YLF material preferably used to fabricate the laser rod 12, the first end 14 is coated for high reflectivity at 1.047 µm. The second end 16 of the laser rod 12 is cut at a Brewster's angle in a manner well known in the pertinent art.

The apparatus 10 also includes a first mirror 18 and a second mirror 20. Together, the laser rod 12, first mirror 18 and second mirror 20 define a folded laser cavity. Specifically, it may be appreciated that light within the laser cavity is focuses to repeatedly traverse an internal beam path 22 between the first end 14 of the laser rod 12, first mirror 18 and second mirror 20. As shown, several components are positioned along the internal beam path 22. These components include: an electro-optical crystal 24, a quarter-wave plate 26, thin-film plate 28, etalon plate 30 and a mode locker 32. The output from the laser cavity is shown and designated 34.

The present invention also includes a laser pumping subsystem 36. The laser pumping subsystem 36 includes a diode laser 38, first collimating lens 40, second collimating lens 42 and focusing lens 44. As shown in FIG. 1, it may be seen that light 46 emitted by the laser diode 38 passes through the first collimating lens 40, second collimating lens 42 and focusing lens 44. Further, it may be seen that light 46 is focused to pass through the first end 14 of the laser rod 12 and impinge upon the Nd:YLF material within the laser rod 12. For the purposes of the present invention, the laser diode 38 may comprise either a single laser diode or, in higher power applications, a laser diode array may be used. Additionally, it should be appreciated that the particular laser pumping subsystem 36 shown in FIG. 1 is intended to be exemplary and that other pumping technologies are equally practical.

OPERATION

Figure 2A:
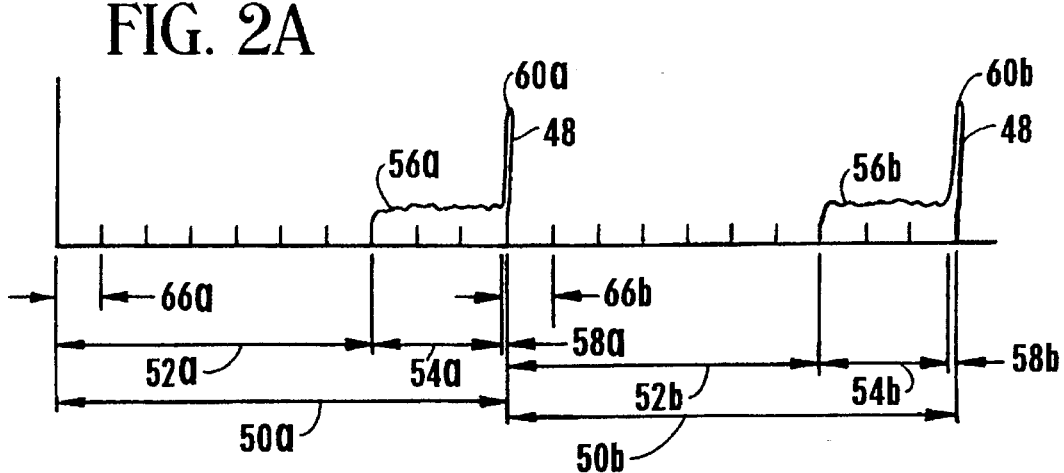
FIG. 2A is a time history depiction of the laser energy level within the laser cavity of the present invention during two working cycles.
Figure 2B:
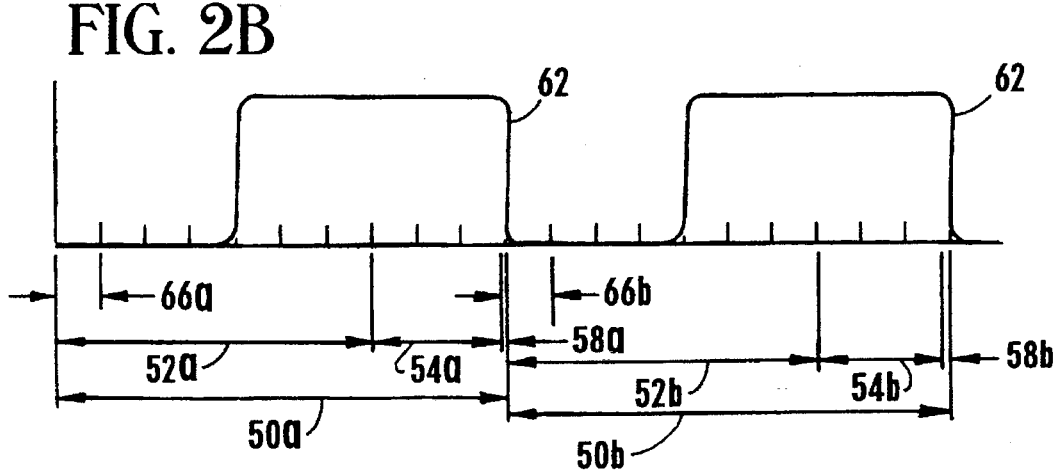
FIG. 2B is a time history depiction of the activation state of the laser pumping means in the laser pulse generator of the present-invention during two working cycles.
Figure 2C:
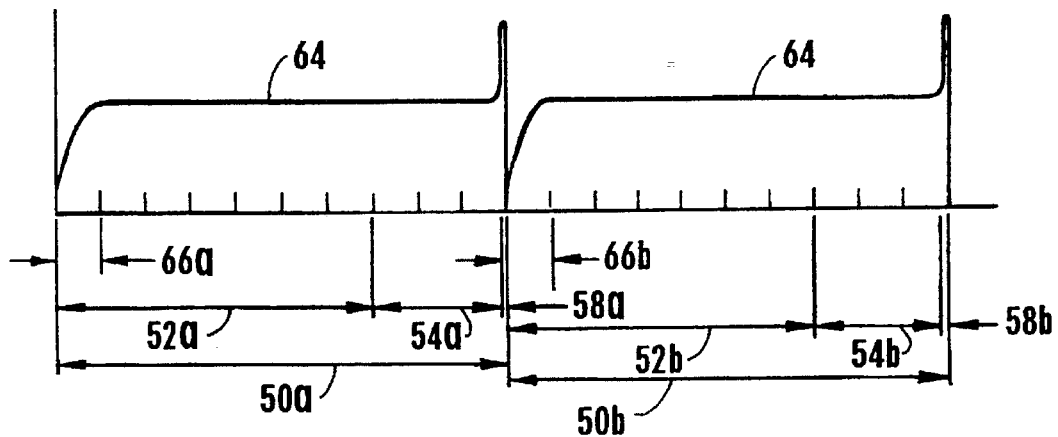
FIG. 2C is a time history depiction of the activation state of the electro-optical crystal during two working cycles in the operation of the present invention.

The operation of the present invention is best appreciated, perhaps, by reference to FIGS. 2A, 2B, and 2C. In FIG. 2A, the waveform which corresponds to the laser energy on beam path 22 plotted as a function of time is shown and designated 48. In greater detail, it may be seen that laser energy waveform 48 is divided into a repeating sequence of working cycles of which the working cycles 50a and 50b are representative. Furthermore, it may be seen that the working cycle 50a, 50b begins with an initial no-lase period 52a, 52b where laser energy waveform 48 is substantially inactive. The no-lase period 52a, 52b corresponds to a low or substantially zero energy level on beam path 22. After the no-lase period 52a, 52b, laser energy waveform 48 enters a pulse-shaping period 54a, 54b characterized by a series of low energy pulses, such as pulse 56a and 56b which traverse beam path 22. A pulse-amplification period 58a, 58b characterized by a high-energy pulse 60a, 60b on beam path 22 ends the working cycle 50a, 50b. In general, the working cycle 50a, 50b shown in FIGS. 2A, 2B and 2C may vary in duration according to the desired frequency with which high-energy pulse 60a, 60b is to be produced. For the purposes of illustration, however, the working cycle 50a, 50b shown in FIGS. 2A, 2B and 2C is chosen to be 1 millisecond in duration and corresponds to a output repetition rate of one-kilohertz (1 kHz).

It may be appreciated that the specific laser energy waveform 48 shown in FIG. 2A is the result of a repeated series of manipulations of the various components of the laser apparatus 10. These manipulations may be seen graphically in FIGS. 2B and 2C where the waveform corresponding to the output of the laser pumping subsystem 36 and the waveform corresponding to the activation state of the electro-optical crystal 24 are plotted as a function of time and designated 62 and. 64 respectively. As shown in FIG. 2B and 2C, the initial no-lase period 52a, 52b begins with the laser pumping subsystem 36 in a state of deactivation. As a result, pumping waveform 62 remains at a zero level. During the same time period, however, the crystal activation waveform 64 undergoes a change in value. More specifically, it may be seen that crystal activation waveform 64 increases from a value of zero at the beginning of the no-lase period 52a, 52b and reaches a predetermined level of partial activation over a period 66a, 66b which corresponds to the rise-time of the electro-optical crystal 24. Physically, the change in crystal activation waveform 64 during period 66a, 66b is caused by application of a predetermined intermediate voltage level to the electro-optical crystal 24. In response to the applied voltage, the electro-optical crystal 24 becomes partially activated after a delay determined by the physical properties of the particular electro-optical crystal employed. Generally, the period 66a, 66b required for the rise time of the electro-optical crystal will be approximately one-hundred microseconds in duration (100 μs).

As shown by pumping waveform 62 in FIG. 2B, the laser pumping system 36 is activated part-way through the no-lase period 52a, 52b. More specifically, a voltage is applied to laser diode 38 and creates a laser output 46. The output 46 is collimated by the first collimating lens 40 and second collimating lens 42 and projected by the focusing lens 44 into the laser rod 12. Generally, the process whereby an energy source is focused on a laser medium, such as laser rod 12, is known as "pumping" and is used to create an electron inversion, or gain, within the laser medium. Once the electron inversion has been created, the laser medium may be used as a regenerative amplifier and a train of laser pulses may be created. Creation of the required electron inversion, however, cannot be accomplished instantaneously and generally requires that the laser medium be pumped for a finite time period before it may be used as a regenerative amplifier. In fact, gain within a laser medium, like laser rod 12, will generally start at a low or zero level and continue to build as the medium is pumped. As a result, or the purposes of the present invention, pumping of the laser rod 12 is initiated approximately three-hundred microseconds (300 μs) before the ending of the no-lase period 52a, 52b.

Once the laser rod 12 has been adequately pumped by the laser pumping subsystem 36, the pulse-shaping period 54a, 54b begins. During the pulse-shaping period 54a, 54b the laser pumping subsystem 36 continues to pump the laser rod 12 increasing the gain within the laser rod 12. As a result, pumping waveform 62 in FIG. 2B remains constant during the pulse-shaping period 54a, 54b. Additionally, the partial activation of the electro-optical crystal 24 remains constant with the result that crystal activation waveform 64 in FIG. 2C remains constant during the pulse-shaping period 54a, 54b. The energy level on beam path 22, however, does not remain constant during the pulse-shaping period 54a, 54b. Instead, a series of low power pulses, of which pulse 56a and 56b are representative, are generated to traverse the beam path 22 between the first end 14 of the laser rod 12, first mirror 18 and second mirror 20.

As pulse 56a and 56b traverse the beam path 22, several transformations occur. In more detail, it may be seen that beam path 22 passes through quarter-wave plate 26. As a result, the phase of pulse 56a and 56b is subject to a quarter-wave (λ/4) rotation. After rotation by a quarter-wave, pulse 56a and 56b pass through the electro-optical crystal 24. As previously discussed, electro-optical crystal is only partially activated during the pulse-shaping period 54a, 54b with the result that the polarity of the electro-optical crystal is less than a quarter-wave. The combination of the quarter-wave rotation provided by the quarter-wave plate 26 and the less-than-quarter-wave rotation provided by the partially activated electro-optical crystal 24 has the result that pulse 56a and 56b are not confined to beam path 22. Instead, a series of low power pulses are ejected from beam path 22 by thin-film polarizer 28. It should be appreciated, however, that energy loss associated with the ejected pulses is relatively low due to the relatively low gain within laser rod 12 during the pulse-shaping period 54a, 54b.

Importantly, beam path 22 also passes through mode locker 32 which functions to shorten the duration of the pulse 56a and 56b. For the purposes of the present invention, it should be appreciated that the mode locker 32 may be of any type generally available which is consistent with the performance requirements of the present invention. Specifically, mode locker 32 may be of any type which allows the pulse shortening function to complete within the approximately two-hundred and fifty to three-hundred microseconds (250 to 300 μs) duration of the pulse-shaping period 54a, 54b.

At the completion of pulse-shaping period 54a, 54b and beginning of the pulse-amplification period 58a, 58b, and as shown in FIG. 2C, a full quarter-wave voltage is applied to the electro-optical crystal 24 causing the pulse 56a and 56b travelling along beam path 22 to be subject a full quarter-wave phase rotation. The phase rotation supplied by the electro-optical crystal 24 combines with the quarter-wave phase rotation supplied by the quarter-wave plate 26 to confine a single pulse 60a, 60b within the laser cavity defined by the laser rod 12, first mirror 18 and second mirror 20. Additionally, the pumping of the laser rod 12 has resulted in a high-gain condition within the laser rod 12. As the pulse 60a, 60b circulates along beam path 22, the high-gain condition in the laser rod 12 causes the pulse 60a, 60b to undergo a rapid amplification. In fact, practice has shown that the amplitude of pulse 60a, 60b will increase by a factor which ranges from several hundred fold to approximately one-thousand fold during the approximately two-tenths of one microsecond (0.2 μs) to one microsecond (1 μs) duration of the pulse-amplification period 58a, 58b.

As the pulse-amplification period 58a, 58b ends, the waveforms 62 and 64 return to the levels present at the start of the working cycle 50a, 50b. Alternatively stated, both the laser pumping subsystem 36 and the electro-optical crystal 24 are deactivated. The deactivation of the electro-optical crystal causes the pulse 60a, 60b to be ejected by the thin-film polarizer 28 along path 34. This ejection becomes the output of the apparatus 10. Accordingly, by repeatedly cycling the apparatus 10 through a series of working cycles 50a, 50b, as disclosed above, a beam of amplified laser pulses is generated on output path 34.

For the purposes of the present invention, it may be appreciated that the duration of the working cycle 50a, 50b may be altered to produce an output, like pulse 60a, 60b, at a desired rate of repetition. Generally, the length of working cycle 50a, 50b may be either lengthened or shorted by increasing or decreasing the length of the no-lase period 52a, 52b. It should be appreciated, however, that shortening no-lase period 52a, 52b to less than approximately three-hundred micro-seconds (300 μs) will decrease the gain available in laser rod 12 during pulse-shaping period 54a, 54b. As a result, there may be some loss in output amplitude of apparatus 10.

While the particular pulsed laser beam generator as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A system for a pulsed laser beam generator having a housing with a cavity defining an internal laser beam path which comprises:

an electro-optical crystal oriented on said internal beam path;

a laser medium;

means for pumping said laser medium;

means for selectively controlling said crystal and said pumping means to establish a three period working cycle for said laser beam generator, said working cycle including an initial no-lase period wherein said crystal is partially activated and said pumping means is deactivated, said no-lase period followed by a pulse-shaping period wherein said crystal is partially activated and said pumping means is activated to allow light from said pumped laser medium to travel along said internal beam path for pulse-shaping in said cavity, said pulse-shaping period followed by a pulse-amplification period wherein said crystal is fully activated and said pumping means is activated to confine light to said path for creation of an amplified laser pulse in said cavity; and means for ejecting said amplified laser pulse from said cavity at the end of said working cycle.

2. A system as recited in claim 1 wherein said electro-optical crystal is a pockel's cell.

3. A system as recited in claim 2 further comprising a quarter-wave (λ/4) plate oriented on said path for cooperating with said pockel's cell to prevent the generation of laser pulses in said cavity when said pockel's cell is deactivated.

4. A system as recited in claim 3 further comprising a polarizing mirror, said polarizing mirror being oriented on said path for cooperation with said quarter-wave plate and said pockel's cell to confine light in said cavity when said pockel's cell is partially or fully activated.

5. A system as recited in claim 1 wherein said laser medium is a Nd:YLF crystal.

6. A system as recited in claim 1 wherein said pumping means is a laser diode.

7. A system as recited in claim 1 wherein said pumping means is an array of laser diodes.

8. A system as recited in claim 1 wherein said working cycle is variable in length with said no-lase period greater than approximately three-hundred microseconds in duration (300 μs), said pulse-shaping period approximately two-hundred and fifty microseconds in duration (250 μs), and said pulse-amplification period approximately two-tenths of one microsecond (0.2 μs) to one microsecond in duration (1 μs).

9. A system as recited in claim 1 wherein pumping means is activated approximately three-hundred microseconds (300 μs) prior to the initiation of said pulse-shaping period.

10. A system as recited in claim 1 wherein said no-lase period, said pulse-shaping period, and said pulse-amplification period may be sequentially repeated at a frequency of one point seven kilohertz (1.7 Khz).

11. A method for generating a pulsed laser beam which comprises the steps of:

a) establishing a beam path between a pair of end mirrors;

b) orienting an electro-optical crystal on said beam path;

c) orienting a laser medium on said beam path;

d) orienting a laser diode array to selectively pump said laser medium;

e) configuring said crystal in a partially activated state and said laser diode in a deactivated state for a predetermined no-lase period;

f) maintaining said crystal in a partially activated state and configuring said laser diode in an activated state for a predetermined pulse-shaping period to direct light from said medium along said beam path and to allow said light to pulse-shape in said cavity;

g) configuring said crystal in a fully activated state and maintaining said laser diode in an activated state for a predetermined pulse amplification period to confine light to said path for creation of an amplified laser pulse in said cavity;

h) deactivating said crystal to eject said amplified laser pulse from said cavity; and i) repeating steps e) through h) to generate said pulsed laser beam.

12. A method as recited in claim 11 wherein steps e) through h) may be sequentially repeated at a variable frequency.

13. A method as recited in claim 11 wherein steps e) through h) may be sequentially repeated at a frequency of one point seven kilohertz (1.7 Khz).

14. A method as recited in claim 11 wherein said no-lase period is greater than approximately three-hundred microseconds in duration (300 μs).

15. A method as recited in claim 11 wherein said pulse-shaping period is approximately two-hundred and fifty microseconds in duration (250 μs).

16. A method as recited in claim 11 wherein said pulse-amplification period is approximately two-tenths of one microsecond (0.2 μs) to one microsecond (1 μs) in duration.

17. A method as recited in claim 11 wherein said laser diode is activated approximately three-hundred microseconds prior to said pulse-shaping period (300 μs).

* * * * *